(12) United States Patent
Lee et al.

(10) Patent No.: US 6,902,748 B1
(45) Date of Patent: Jun. 7, 2005

(54) **MEDICINES MANUFACTURED FROM OLD *PLATYCODON* EXTRACTS**

(75) Inventors: Sung-Ho Lee, Chinju (KR); Young-Chun Lee, Chinju (KR); Young-Chul Jung, Chinju (KR); Jong-Kwon Seo, Chinju (KR); Jong-Su Noh, Ulsan (KR)

(73) Assignee: Jang Saeng Doraji Co., Ltd, Chinju (KR)

( * ) Notice: Subject to any disclaimer, the term of this patent is extended or adjusted under 35 U.S.C. 154(b) by 0 days.

(21) Appl. No.: 10/168,450

(22) PCT Filed: Dec. 22, 1999

(86) PCT No.: PCT/KR99/00803

§ 371 (c)(1),
(2), (4) Date: Jun. 21, 2002

(87) PCT Pub. No.: WO01/45723

PCT Pub. Date: Jun. 28, 2001

(51) Int. Cl.[7] ............................................... A61K 35/78
(52) U.S. Cl. ...................................................... 424/769
(58) Field of Search ........................... 435/769; 424/769

(56) References Cited

FOREIGN PATENT DOCUMENTS

| JP | 60-089427 | 5/1985 |
|----|-----------|--------|
| JP | 02-172921 | 4/1990 |
| JP | 03-264534 | 11/1991 |
| KR | 1991-0006203 | 8/1991 |

OTHER PUBLICATIONS

Computer Derwent Abstract 1992–035906 JP 03280854 "New immuno–activating liquid and solid compsns–comprises at leat one of Allium odorum, roots of platycodon grandiflorum and a chinese matriomony vine" Dec. 1991.* Computer.*

Eun Bang Lee, "Pharmacological Studies on 'Platycodi Radix'," Herbal Medicine Academic Paper, 5, 49 (1974).

Hiroshi Hitokoto, et al. "Inhibitory Effects of Condiments and Herbal Drugs on the Growth and Toxin Production of Toxigenic Fungi", Mycopathologia 66,3: 161–167 (1978).

Michinori Kubo, et al. "Immune Pharmacological Studies on Platycodi Radix (I) Effect on the Phagocytosis in Mouse," Shoyakugaku Zasshi 40(4), 367–374 (1986).

Takaharu Nagao, et al. "Immune Pharmacological Studies on Platycodi Radix (II) Antitumor Activity of Inulin from Platycodi Radix," Shoyakugaku Zasshi 40(4), 375–380 (1986).

* cited by examiner

*Primary Examiner*—Herbert J. Liling
(74) *Attorney, Agent, or Firm*—Park & Sutton LLP; John K. Park (57) ABSTRACT

The present invention relates to antibiotics, anti-inflammatory agents, antihyperlipidemia agents, antidiabetes agents and anticancer agents, of which medical treatment materials are extracted by hot water or organic solvent from 20-year (or older) perennial old *platycodon* (i.e., old *platycodon*) with various physiological effects, or selective mixture of these extracts and other allowable herbal medicines or herbal medicine extracts. The old *platycodon* extracts have further enhanced effects than conventional medicines or 2–4 year old common *platycodon*, in terms of antibiotic activity, lipid metabolism improving activity, blood glucose level lowering activity, inhibition activity against adhesion of cancer cells immunity increasing effect, anti-arthritis effect, etc.

8 Claims, 4 Drawing Sheets

MEDICINES MANUFACTURED FROM OLD *PLATYCODON* EXTRACTS

TECHNICAL FIELD

The present invention relates to antibiotics, anti-inflammatory agents, anti-hyperlipidemia agents, anti-diabetes agents and anticancer agents, manufactured using an old *platycodon* extract, based on various pharmacological effects of 20-year (or older) old *platycodon* produced in accordance with 'A guide for growing perennial *platycodon*'.

BACKGROUND OF THE INVENTION

*Platycodon* (*Platycodon grandiflorum* A.DC), which has been used as a herbal medicine for respiratory diseases such as the expulsion of discharge, expulsion of sputum, bronchitis, asthma, anti-inflammation, among others, is known to have various medical effects; as many as 273 herbal prescriptions mixed with *platycodon* are recorded in the Oriental Medicine Handbook, and 49 prescriptions are recorded in the Oriental Medicine Book (Bang-Yak-Hap-Pyun in Korean).

Terpenoid saponins (18 kinds including platyconin A, C, D, D6, polygalasin D, D2, etc.), which produce the major pharmacological effects of *platycodon*, compose 2% of the root. In trials on animals, Terpenoid saponins has proved to have be effective for hemolysis, local stimulation, suppression of coughs, expulsion of sputum, central nervous suppression activity (tranquilization, analgesic, antipyretic effect), anti-inflammation for acute/chronic inflammation anti-allergy, anti-ulcer, and inhibitory action for gastric juice secretion, anti-cholinergic which lowers blood pressure level by extending the blood vessels, blood glucose level lowing activity, and lipid metabolism improving activity, etc. (Igarashi, K., Sogoigaku, 3, 1(1951) and Lee En Bang, Herbal Medicine Academic Paper, 5, 49(1974)). In addition, steroid compound such as alpha-spinasterol, stigmaste-7-enol, alpha-spinasterolglucosid, etc. and polysaccharide such as inulin, platycodinin and betulin, were separated into single components.

The hot water and methanol extract of *platycodon* suppress aflatoxin of fungi (Hitokoto, H., Morozumi, S., Wake, T., Kakai, S. and Ueno, L., Mycopathologia, 66, 161(1979)), and inulin fraction is known to have phagocytosis (Nagao, T., Matsuda, H., Nambo, K. and Kubo, M., Shoyakugaku Zasshi, 40, 367(1986)) while inulin, the fructose polymer, is known to have an anti-cancer effect on solid cancer and complicated or complex cancer (Naga, T., Matsuda, H., Makata, K., Namba and Kubo, M., Shoyakugaku Zasshi, 40, 375(1986)).

The recently developed anti-tumor medicine is being applied to clinical experiments. However, although chemotherapeutics shows clinical effects, it is often accompanied by significant side effects. For example, mytomicin C causes a side effect of renal failure, and adryamicin and carbazilquinon causes a side effect of bone marrow suppression. Therefore, it is strongly recommend to have antitumor agents that are safe as well as strong anti-tumor suppression actions for oral administration.

Japanese Patent Publication No. 60-89427 discloses that the inulin fraction out of the *platycodon*'s 70% methanol extract, has 31–39% and 32–44% suppression effect on complicated cancer and solid cancer of each ICR mice, and when administered in parallel with mytomicin, a chemotherapeutic, it not only suppresses solid cancer by up to 61% but also prevents a decrease in body weight and the number of leucocytes, the side effect of mytomicin. Japanese Patent Publication No. 3-264534 introduces 40% *platycodon* extract as a material suppressing alcohol absorption.

Currently, over 30 kinds of herbal medicinal products containing *platycodon* are available on the markets in Korea, China, Japan, etc.; "O-Yak-Soon-Gi-powder", "Tong-Gi-tablet", "Soon-Gi-Won", etc. are used as agents against paralysis, arthritis, etc., "An-Shim-Won" and "Choen-Wang-Bo-Shim-Dan" as agents against high blood pressure, brain disease, etc,. "Ja-Mo" extract as agents against bronchitis, tuberculosis, pleurisy, etc., "Man-Ok-Dan" as agents against high blood pressure, arteriosclerosis, diabetes, etc. Herbal medicines containing *platycodon*, other than these, are used to cure related bronchus diseases such as asthma, expulsion of sputum, expulsion of discharge, suppression of cough, etc.

Thus far, however, *platycodon* has been used for the above herbal medicine materials and for experiments using only 2–4 year old plants because their roots become rotten 4–5 years after planting. The 20-year (or older) perennial old *platycodon*, produced in accordance with the 'A guide to growing perennial *platycodon*' recently patented (No. 45791), is a patent protected herbal medicine, and is not used at all for herbal medicines.

Accordingly, the present inventors have successfully developed its usage as medicines, such as in the form of health food and herbal medicines, by using the superiority of the old *platycodon* over the 2–4 year old ordinary *platycodon* in terms of pharmacological effects.

SUMMARY OF THE INVENTION

An object of the present invention is to provide a usage for old *platycodon* as a herbal medicine, which has excellent pharmacological effects and physiological activity as compared with 2–4 year old ordinary *platycodon*.

Another object of the present invention is to provide antibiotics using the extract of old *platycodon*.

A further object of the present invention is to provide agents against hyperlipidemia using the extract of old *platycodon*. A still further object of the present invention is to provide agents against diabetes using the extract of old *platycodon*.

A still further object of the present invention is to provide agents against cancer with inhibitory activity against the adhesion of cancer cells and immunity increasing effect using the old *platycodon* extract.

A still further object of the present invention is to provide herbal medicine which is toxicity-free and free from any other side-effects in the living body.

The present invention relates to antibiotics, anti-inflammatory agents, antihyperlipidemia agents, anti-diabetes agents and anticancer agents, of which medical treatment materials are extracted by hot water or organic solvent from 20-year (or older) perennial old *platycodon* (i.e., old *platycodon*) with various physiological effects, or selective mixture of these extracts and other allowable herbal medicines or herbal medicine extracts. The old *platycodon* extracts have further enhanced effects than conventional medicines or 2–4 year old common *platycodon*, in terms of antibiotic activity, lipid metabolism improving activity, blood glucose level lowering activity, inhibition activity against adhesion of cancer cells, immunity increasing effect, anti-arthritis effect, etc.

The foregoing and other objects of the present invention will become more apparent in light of the following descrip-

DESCRIPTION OF THE PREFERRED EMBODIMENTS

The present invention concerns a usage of the extract as antibiotics, anti-hyperlipidemia agents, anti-diabetes agents, anticancer agents or anti-inflammation agents, which is extracted by boiling water or by organic solvent, after converting the old *platycodon* to powder. The difference in terms of components and pharmacological effects between ordinary *platycodon* and old *platycodon* will be described in detail.

There is no significant difference between ordinary *platycodon* and old *platycodon* in moisture content, crude fat, inorganic salt, etc. 22-year old *platycodon* is found to have 3.1% and 0.4% more total amount of dietary fiber and crude saponin, respectively compared to ordinary *platycodon*. Although there is almost no difference between the two in the total amount of Inulin, 70–73 mg/g, *platycodon*'s saccharine components, there is a big difference in polymerization of fructose, Inulin components, between the two. That is, the fact that old *platycodon* has relatively rich concentrations of G-$F_2$ and G-$F_3$ while ordinary *platycodon* has relatively richer concentrations of G-F5 and G-F8 indicates a significant difference between the two *platycodon* in terms of the structure of inulin. G referred to in the above means Glucose, F means fructose; these represent the composing properties of Inulin, and the quantity of fructose is expressed as a number. As for the degree of fructose polymerization of Inulin, the longer the growth length is, the higher the level of Oligofructose detected with a low fructose number. This result is presumably linked to the clinical trial result where old *platycodon* has a greater effect than ordinary *platycodon* on high blood pressure, bronchitis, diabetes, etc.

The contents of inorganic salt such as Ca, Mg, Cu are 3–10 times higher in old *platycodon* than ordinary *platycodon*.

The analysis with HPLC of 80% Ethanol and 30% methanol extracted from ordinary *platycodon* and old *platycodon* each shows a difference in content for one and two peaks. The peak, which is obviously present in old *platycodon* only, was again fractionated by organic solvent according to polarity to investigate the physiological activity. It was proved that it is of steroid material when analyzed through various analyzing devices following the recognition of effect of petroleum ether- and diethyl ether-fraction.

Old *platycodon* not only shows a significant difference from ordinary *platycodon* in its composing properties, but also has far greater pharmacological effect than ordinary *platycodon* in antibiotic activities, lipid metabolism improving effects, inhibition effects against the adhesion of cancer cells, immunity increasing effect, blood glucose level lowering actions, anti-arthritis effect, etc. 80% ethanol and 30% methanol extract of old *platycodon* have the free radical scavenging activity and antibacterial suppression activity without toxicity on cells. Old *platycodon* show a relatively wider range and better antibacterial spectrum. Ethanol extract of old *platycodon* indicates an MIC value of 5 mg/ml for bacteria and 2,5–10 mg/ml for protozoa. Antibaterial active materials is easily extracted at 50° C. at the concentration of 95% Ethanol. When 95% ethanol extract of old playcodon was again fractionated by organic solvent, the antibacterial activity was found to at the highest level in buthanol fraction. This result is presumably attributable to saponin properties, and it is inferred that the antibacterial activity material is more than two from the activity detected in other organic solvent fraction. A structural analysis using various devices, separated from ethyl acetate fraction out of antibacterial activity material of old *platycodon*, indicates the structure is glyceril linolate.

In case the powder or extract of old *platycodon* is fed to the mice causing hyperlipidemia, blood serum, blood glucose and lipid of liver are dramatically decreased. The group to which 5% powder of old *platycodon* showed a dramatic decrease in total cholesterol amount and level of triglyceride in blood serum and liver, and at the same time a decrease in the index of arteriosclerosis, also showed a relatively low level, compared to the group which was not fed by old *platycodon*. Such results suggest the allowable prescription of old *platycodon* in suppressing and curing high cholesterol level or hyperlipidemia.

The old *platycodon* extract discussed in the present invention is useful in curing diabetes because it has a greater effect than ordinary *platycodon* on lipid profile improvement of blood glucose, serum, and liver, etc. The old *platycodon* extract decreases serum total cholesterol and LDL level by a significant level, while it increases serum HDL-cholesterol level. It decreases serum free cholesterol, cholesterol ester, triglyceride and phospholipid level to a low level, thus lowering the index of arterioscleroiss as well.

When the old *platycodon* extract is treated to cancer cell line, the inhibitory activity against the adhesion of cancer cells appears to be excellent. When the methanol extract of the old *platycodon* is treated on B16-F1 mice melanoma cell to measure the adhesion degree of Laminin, 100% inhibitory activity against the adhesion of cancer cells appears in cancer cell line when the concentration of the extract is above 0.125 mg/ml. By this, it is understood the old *platycodon* suppresses cancer transfer even at the low concentration.

Also, when the old *platycodon* extract fraction is investigated for Immunity increasing activity according to solvent polarity, the best effect is shown in the layer of aqueous solution. The analysis of this aqueous layer using HPLC shows that the best immunity increasing activity is detected in the inulin fraction with less than 20 of polymerization of fructose in inulin. It is assumed that the result which indicates 5 times higher immunity increasing activity of old *platycodon* than ordinary *platycodon* is closely correlated with fructose polymerization of inulin.

Since the old *platycodon* extract functions to suppress edema, it can also be used to treat inflammation such as rheumatic arthritis. It shows an edema suppression effect equivalent to predisolone, the present edema suppressing agents. The allowable mixtures of herbal medicines or herbal medicine extract which can activate the effect of old *platycodon*, and the old *platycodon* extract increases the edema suppression activity due to the synergistic effect.

In the present invention, health food and medicinal stuffs using such excellent pharmacological effects of old *platycodon* are provided. The extract, which can be used for health food and medicinal stuffs using old *platycodon* of the present invention, is treated in accordance with the customary method in this field. The old *platycodon* extract is usually referred to as boiling water extract and organic solvent extract, and these extracts may be exclusively used and manufactured after addition of herb medicines.

In general, to produce the old *platycodon* powder, the old *platycodon* is dried to less than 5% water contents and ground to grains with a size of less than 0.6 mm for the final manufacturing process. Boiling water extract is mixed with the perennial *platycodon* powder to which 5–10 times of water, and 2 times of extracting process is added at 90–100 iÉ for 4–6 hours to obtain a filtered extract. Possible herb medicine or herb medicine extract is selectively added to this filtered extract to produce the final product. In case of organic solvent extract, about 3 times of organic solvent is added to the old *platycodon* powder, and 2 times of extracting process is made at room temperature. The filtered liquid from this process is decompressed, concentrated and mixed with allowable herb medicine or herb medicine extract which are selectively added to produce the final product.

Preferably, alcohol or methanol/ethanol is used as the above-mentioned organic solvent. Preferably, herb medicine includes Atractylodis Rhizoma (*Atractylodes japonica*), Crataegi Fructus (*Crataegus pinnatifida*), polygalae radix (*polygala tenuifolia*), *polygonum multflorum*, Hoelen and the like.

Old *platycodon* extracts of the present invention are made into health products or medicines in a widely known method using allowable solvent, and then pressured into containers by unit amount or bulk amount. Heath food or medicine may be in the form of aqueous solution, suspension or emulsion, or in the form of extract, powder, granule, tablet and capsule, and they may contain common diversion material, suspension material or suppression material.

Pharmacological effects of the old *platycodon* extract manufactured using the above-described method, or the old *platycodon* extract mixed with other allowable herb medicine, such as antibiotic activity, lipid metabolism improving activity, blood glucose level lowering activity, inhibition activity against adhesion of cancer cells, immunity increasing effect, anti-arthritis effect, etc. were detected in the following experiments.

The present invention will be more apparent by the following embodiments thereof, without limiting the scope of the present invention.

EXAMPLES

Example 1

Manufacture of Herb Medicines Using Old *Platycodon*

Old *platycodon* is dried to below 5% water contents and ground to produce grains with a size of less than 0.6 mm to manufacture the powder. Subsequently, water, an amount of which is 10 times larger than the powder, is added to the powder, and an extracting process is made 2 times at a temperature of 90–100° C. for 4–6 hours to obtain a filtered liquid. The filtered liquid is packaged into a liquid product. The filtered liquid is further concentrated to manufacture undiluted liquid, powder, granule, capsule and herbal medicine ball-type tablet.

1 kg of old *platycodon* is ground, extracted using 4 L of ethanol at room temperature for 2 times during 2 days, and the resultant substance is filtered. Then, the filtered liquid is decompressure-concentrated so as to produce 125 g of ethanol extract. Using this extract, undiluted liquid, powder, granule, capsule and herbal medicine ball-type tablet may be produced.

In order to increase the pharmacological effect, preferable herbal medicinal materials such as Atractylodis Rhizoma (*Atractylodes japonica*), Crataegi Fructus (*Crataegus pinnatifida*), polygalae radix (*polygala tenuifolia*), *polygonum multflorum*, Hoelen or herb medicine extracted in the manner same as above, can be added to the old *platycodon* extract.

Example 2

Anti Bacterial Activity Test on, Old *Platycodon*

In this embodiment, an antibacterial activity test is performed by measuring MIC (minimum inhibition concentration) of ethanol extract of old *platycodon* treated on 14 kinds of food decay (food poisoning) microorganism and disease causing microorganism. Using 96-well plate, absorbance of each cell line is controlled to become 0.5 at 660 nm, and the *platycodon* extract is added to medium by concentration to culture for 24 hours at a temperature of 37 C. Then, the MIC at this time is measured in such a way and the degree of growth is shown in Table 1. The Muller Hinton medium is used to confirm bacteria while malt extract medium was used to confirm mold.

TABLE 1

| microorganism | Platycodon Minimum inhibition concentration (mg/ml) Broth | Platycodon Minimum inhibition concentration (mg/ml) Agar | Old platycodon Minimum inhibition concentration (mg/ml) Broth | Old platycodon Minimum inhibition concentration (mg/ml) Agar |
| --- | --- | --- | --- | --- |
| B. subtilis | 20.00 | 10.00 | 5.00 | 2.50 |
| M. luteus | 20.00 | 10.00 | 5.00 | 2.50 |
| S. epidermidis | 40.00 | 20.00 | 10.00 | 5.00 |
| E. coli | 80.00 | 40.00 | 10.00 | 5.00 |
| K. pneumoniae | 80.00 | 40.00 | 10.00 | 5.00 |
| P. aeroginosa | 160.00 | 40.00 | 20.00 | 5.00 |
| S. typhi | 20.00 | 10.00 | 2.50 | 2.50 |
| V. parahaemolyticus | 40.00 | 20.00 | 5.00 | 5.00 |
| C. albicans | 160.00 | 20.00 | 20.00 | 5.00 |
| S. cerevisiae | 40.00 | 20.00 | 10.00 | 5.00 |
| A. flsvus | 160.00 | 40.00 | 20.00 | 5.00 |
| A. niger | 80.00 | 160.00 | 10.00 | 5.00 |
| M. audouinii | 80.00 | 40.00 | 10.00 | 5.00 |
| T. mentagophytes | 80.00 | 80.00 | 10.00 | 10.00 |

Example 3

Effect of the Acute Transfer of Old *Platycodon* on the Blood Serum and Liver Lipid Metabolism of White Mice Causing Hyperlipemia Sprague Dawley white mice weighing 70±5 g were fed with basal diet with 20% casein plus 20% lipid and sodium cholate 0.25% for 2 weeks to cause hyperlipidemia to them. Then, the mice with hyperlipidemia were divided into A, B and C groups, 6 mice each, for experimental growth for 3 weeks. Group A was fed with ordinary feed only (comparative group), Group B was fed with a mixture of 5% ordinary *platycodon* powder, and Group C was fed with a mixture of 5% old *platycodon* powder. In order to compare the effects among the groups, 6 ordinary white mice (Group D) of 4-week old, weighing 70±5 g, were fed with ordinary feed. The old *platycodon* and the ordinary *platycodon* used for the experiments were lyophilized to grind into powder of less than 0.59 mm, and mixed with ordinary feed so it could be supplied to the ordinary mice. The increase in the weight after 3-week intake is shown in Table 2. On the last day of the 3-week experimental growth period, the mice were fasted for 7 hours and blood was extracted (blood obtaining method from the heart) under ether anesthesia. The wet of liver was wiped out with filter paper after removing blood via portal vein with 0.9% physiological saline, and after the blood was left in an ice-water for about 1 hour, blood serum was collected by performing a centrifugal separation at 3,000 rpm for 15 minutes. Then, the blood serum, blood glucose, cholesterol, neutral lipid (triglyceride), phospholipid, GOT (glutamic oxaloacetic tranaminase), GPT (glutamic pyruvic transaninase) and LDH (lactate dehydrogenase) were measured. The results are shown in Table 2. These blood glucose, cholesterol, lipid and enzyme activity were measured using a measuring kit reagent commonly used in the field.

was lower than that of the mice which did not develop hyperlipidemia. Therefore, it can be inferred that the old *platycodon* powder has a preventive and curing effect on hyperlipidemia.

Example 4

Effect of the Old *Platycodon* Extract on Blood Glucose and Lipid of White Mice with Diabetes Alloxan monohydrate (15 mg/kg B.W/day) was injected intraperitoneally (I.P. injection) to 4-week old Sprague Dawley white mice weighing 70±5 g so as to make the mice contract diabetes. The experimental animal groups were divided into A, B and C; each group with 6 mice has been freely fed for 3 weeks according to the food intake of each experimental group. Group A was fed with ordinary feed only (control group), group B was fed with a mixture with 6-year *platycodon* extract, and group C was fed with a mixture with the old *platycodon* (22-year or older) extract. In order to compare the effects among the groups, 6 ordinary white mice (group D) of 4-week old, weighing 70±5 g, were fed with ordinary feed. To obtain the *platycodon* extract for use in the experiments, water was added to 200 g of lyophilized *platycodon* to become IL in total. This was concentrated to 700 ml, and 800 ml of water was poured in again to the residue, and extracted by boiling water to reach

TABLE 2

| Properties | Experimental Group | | | |
|---|---|---|---|---|
| | Group A | Group B | Group C | Group D |
| Weight increase (g/3 weeks) | 352 ± 6.1 | 330 ± 2.8 | 329 ± 5.2 | 346 ± 5.2 |
| Serum | | | | |
| Blood glucose (mg/dl) | 158 ± 5.5 | 156 ± 5.5 | 141 ± 1.4 | 142 ± 3.8 |
| Total cholesterol (mg/dl) | 262 ± 6.4 | 243 ± 2.3 | 166 ± 3.8 | 168 ± 6.0 |
| LDL-cholesterol (mg/dl) | 137 ± 4.3 | 124 ± 5.0 | 74.5 ± 3.0 | 94.4 ± 2.8 |
| HDL-cholesterol (mg/dl) | 62.7 ± 2.5 | 61.4 ± 2.5 | 65.9 ± 2.6 | 52.5 ± 2.3 |
| Free cholesterol (mg/dl) | 45.0 ± 0.6 | 44.2 ± 5.3 | 37.2 ± 1.5 | 31.8 ± 0.9 |
| triglyceride (mg/dl) | 270 ± 12.0 | 256 ± 4.4 | 129 ± 5.0 | 174 ± 5.3 |
| Lipid (mg/dl) | 188 ± 3.3 | 171 ± 3.8 | 118 ± 5.4 | 160 ± 4.7 |
| Index of arteriosclerosis | 3.2 ± 0.3 | 2.8 ± 02 | 1.5 ± 0.1 | 2.2 ± 0.2 |
| GPT (Karmen unit/ml) | 45.7 ± 2.1 | 40.2 ± 2.5 | 29.5 ± 5.1 | 35.6 ± 8.3 |
| GOT (Karmen unit/ml) | 90.1 ± 2.5 | 89.3 ± 3.1 | 80.7 ± 1.3 | 82.5 ± 3.3 |
| LDH (Wroblewski unit/ml) | 1.067 ± 23.7 | 1.347 ± 51.2 | 1.329 ± 53.5 | 1.474 ± 40.6 |
| Liver | | | | |
| Total cholesterol (mg/g) | 17.8 ± 2.8 | 16.1 ± 2.8 | 12.4 ± 3.2 | 8.0 ± 1.7 |
| Free cholesterol (mg/g) | 4.8 ± 0.4 | 5.4 ± 2.1 | 5.1 ± 0.4 | 4.0 ± 0.6 |
| triglyceride (mg/g) | 88.1 ± 2.1 | 78 ± 3.5 | 46.0 ± 3.5 | 73.5 ± 2.3 |
| Lipid (mg/g) | 25.1 ± 4.1 | 25.0 ± 1.4 | 22.4 ± 3.0 | 23.7 ± 3.5 |

Group A: Intake Group fed with ordinary feed, causing hyperlipidemia

Group B: Intake Group fed with feed mixed with 5% ordinary *platycodon* powder

Group C: Intake Group fed with feed mixed with 5% old *platycodon* powder

Group D: Group which does not cause hyperlipidemia

It can be seen that group C, causing hyperlipidemia and fed with old *platycodon* powder, shows even lower level of total cholesterol and triglyceride of serum and liver than the control group (group A) or group B, fed with the ordinary *platycodon* powder. The index of arteriosclerosis of group C 300 ml of final product. On the last day of the 3-week experimental incubation, the mice were fasted for 7 hours and blood was obtained (blood obtaining method from the heart) under ether anesthesia. The moisture of the liver was eliminated with filter paper after removing blood via portal vein with 0.9% physiological saline, and after the blood was incubated in ice-water for about 1 hour, serum was collected by centrifugation at 3,000 rpm for 15 minutes. In the above-mentioned blood serum and liver, blood glucose, cholesterol, triglyceride, phospholipid, AST (aspartate aminotransferase), ALT (alanine aminotransferase) and LDH (lactate dehydrogenase) were measured. The results are recorded in Table 3. These blood glucose, cholesterol, lipid and enzyme activity were measured using measuring kit reagent commonly used in the field.

TABLE 3

| Properties | Experimental Group | | | |
|---|---|---|---|---|
| | Group A | Group B | Group C | Group D |
| Serum | | | | |
| Weight increase (g/3 weeks) | 30 ± 1.4 | 338 ± 5.1 | 328 ± 4.5 | 352 ± 4.3 |
| Blood glucose (mg/dl) | 306.8 ± 19.7 | 271.6 ± 13.2 | 227.5 ± 14.1 | 162.4 ± 9.4 |
| Total cholesterol (mg/dl) | 127.4 ± 5.1 | 104.7 ± 4.5 | 95.9 ± 3.9 | 86.5 ± 3.3 |
| LDL-cholesterol (mg/dl) | 203.8 ± 12.8 | 181.6 ± 13.1 | 163.3 ± 12.7 | 140.5 ± 9.6 |
| HDL-cholesterol (mg/dl) | 16.7 ± 1.6 | 17.3 ± 1.8 | 19.0 ± 1.5 | 23.3 ± 1.3 |
| Index of arteriosclerosis | 6.6 | 5.1 | 4.0 | 2.7 |
| Free cholesterol (mg/dl) | 20.0 ± 0.8 | 15.0 ± 0.9 | 14.6 ± 0.7 | 12.9 ± 0.5 |
| Cholesterol ester (mg/dl)[1] | 107.4 ± 3.2 | 89.7 ± 3.4 | 81.3 ± 2.9 | 73.6 ± 2.5 |
| Cholesterol ester ratio (%)[2] | 84.3 | 85.6 | 84.8 | 85.1 |
| Triglyceride (mg/dl) | 104.6 ± 3.4 | 92.5 ± 3.0 | 86.1 ± 2.9 | 75.3 ± 2.6 |
| Phospholipid (mg/dl) | 148.9 ± 5.2 | 136.5 ± 3.8 | 129.4 ± 4.2 | 115.2 ± 4.7 |
| Liver | | | | |
| Total cholesterol (mg/g) | 8.4 ± 0.3 | 7.3 ± 0.3 | 6.4 ± 0.2 | 5.1 ± 0.2 |
| Triglyceride (mg/g) | 41.5 ± 2.2 | 35.2 ± 2.1 | 32.4 ± 2.2 | 28.7 ± 1.4 |
| Phospholipid (mg/g) | 20.8 ± 1.0 | 18.2 ± 1.1 | 17.5 ± 1.2 | 12.6 ± 0.7 |

[1] Cholesterol ester = total cholesterol − free cholesterol
[2] Ratio of cholesterol ester = Cholesterol ester/total cholesterol × 100

Group A: group with diabetes caused by alloxan, but not treated by the *platycodon*
Group B: group treated with 6-year old *platycodon* boiling water extract
Group C: group fed with 22-year old *platycodon*
Group D: group which is not treated with alloxan As recorded in the above Table 3, blood glucose level was higher in the groups A, B and C fed with alloxan than group D not fed with alloxan. However, groups B and C (treated with the *platycodon* extract) show lower blood glucose levels than group A (control group), and group C (treated with the old *platycodon* extract) showed the lowest level of blood glucose.

Groups B and C showed lower serum total cholesterol and LDL level than group A, and group C showed much lower level than group B, the closest to group D (not fed with alloxan) in its value. Serum HDL-cholesterol level was higher in the groups fed with the *platycodon* extract (groups B and C) than in group A, and group C showed lower level than group B, the closest to group D (not fed by alloxan) in the value. Index of arteriosclerosis was lower in groups B and C than in group A. Serum free cholesterol, cholesterol ester, triglyceride and lipid level were lower in all the groups than in group A. Total cholesterol, triglyceride and lipid in liver, were lower in all the groups than in group A. Group A showed the highest level of blood serum AST, ALT and LDH enzyme activity among all the groups. The results indicate that the *platycodon* extract has pharmacological effects on improvement of the lipid of blood serum, blood sugar and liver, and the old *platycodon* extract in particular has even greater effects.

Example 5

Inhibitory Activity of Old *Platycodon* Against the Adhesion of Cancer Cells

Melanoma cell line of B16-F1 mice were treated with the ethanol extract of old *platycodon*, and the inhibitory activity against the adhesion of cancer cells of old *platycodon* was investigated by measuring quantitatively whether it inhibits the adhesion on laminin which is a kind of matrix of cell. The incubation of the above melanoma cell line was maintained at the minimum required medium [MEM (minimum essential medium), containing Hank's salt], containing fetal bovine serum [FCS (fetal calf serum), 10%]. For laminin-coated plate, 1 mg laminim was resolved in 2 ml of PBS [phosphate buffer saline, NaCl 8 g, KCl 0.2 g, NaHPO$_4$, KH$_2$PO$_4$ 0.24 g/L] and kept in the refrigerator. When necessary, it was diluted with cold PBS solution with a concentration (20 µg/ml) of laminin, and 50 µl of this liquid was added to each well of a 96-well microplate, and dried for a night before use.

To make the cell suspension, 80% confluence and matured B16-F1 cells in T-25 culture flask were removed with 3 ml of 2 mM EDTA solution, and 5 ml of serum-free MEM was added to it. The cell obtained by centrifugation at 800 rpm for 5 minutes was suspended to the appropriate amount of serum-free MEM containing 1% BSA to the cell number of 2×106 cells/ml and the 50 µl of this suspension was used.

To measure the activity, after laminin-coated well was washed 3 times with 100 µl PBS, 100 µl of 1% BSA solution (dissolved in PBS) was added, and BSA was removed under depressurized conditions. On this plate, 50 µl serum-free MEM containing 0.1% BSA, reagents and cells were added, and it was cultured at 37° C. for 1 hour under 5% CO$_2$. After incubation, it was washed with PBS (37° C.) twice, and then washed first with 100 µl of 0.5% BSA (dissolved in PBS) and then 100 µl of PBS. Then the adhesive cells were fixed with 40 µl of 2.5% glutaraldehyde at room temperature for 30 minutes.

Figure 1:
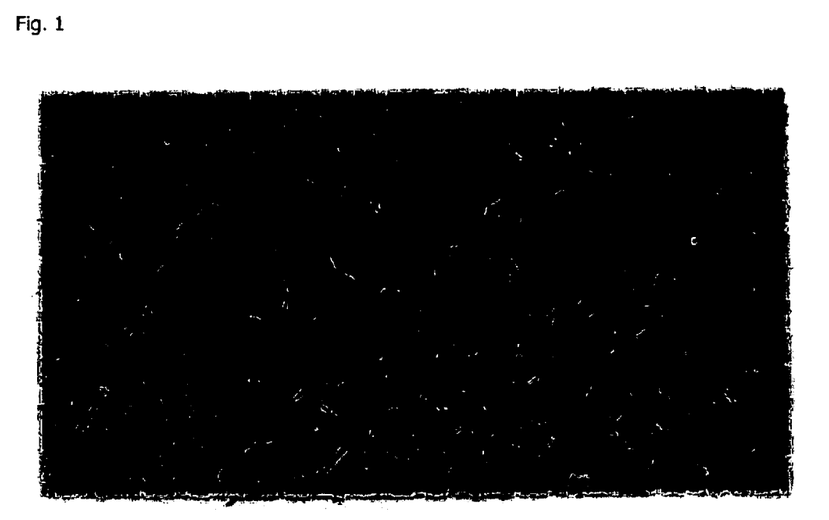
FIGS. 1~7 show microscopic observations of the cell morphology of cancer cell laminin combined with the extract, and the cell morphology when the cell line of B16-F1 melanoma mice is treated with the methanol extract of old *platycodon* at a concentration of 0.031, 0.062, 0.125, 0.25, 05 and 1 mg/ml for one hour.
Figure 2:
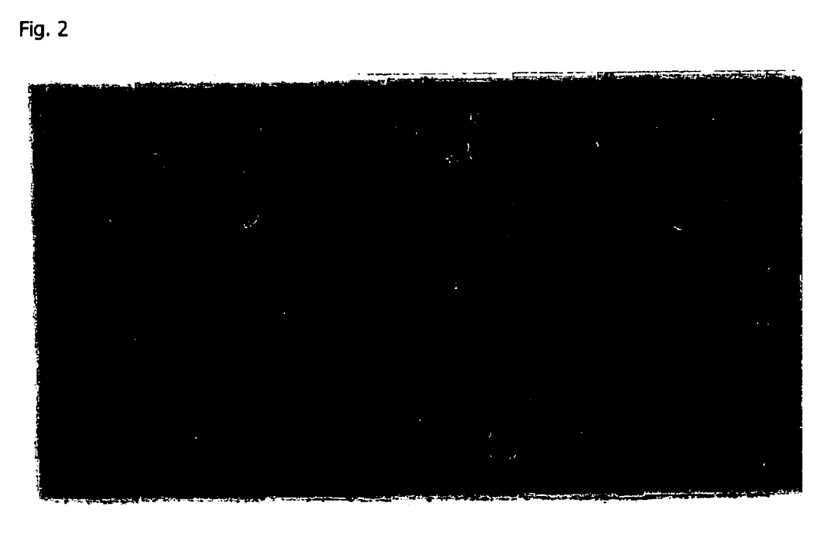
Figure 3:
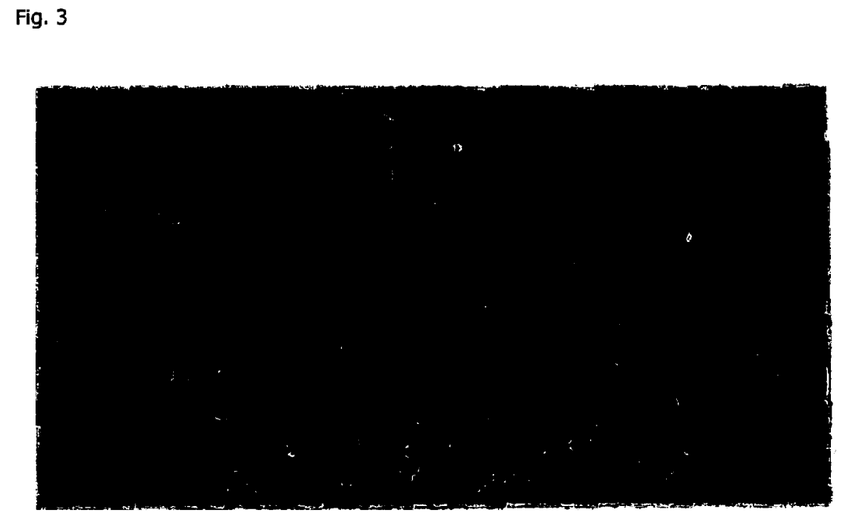
Figure 4:
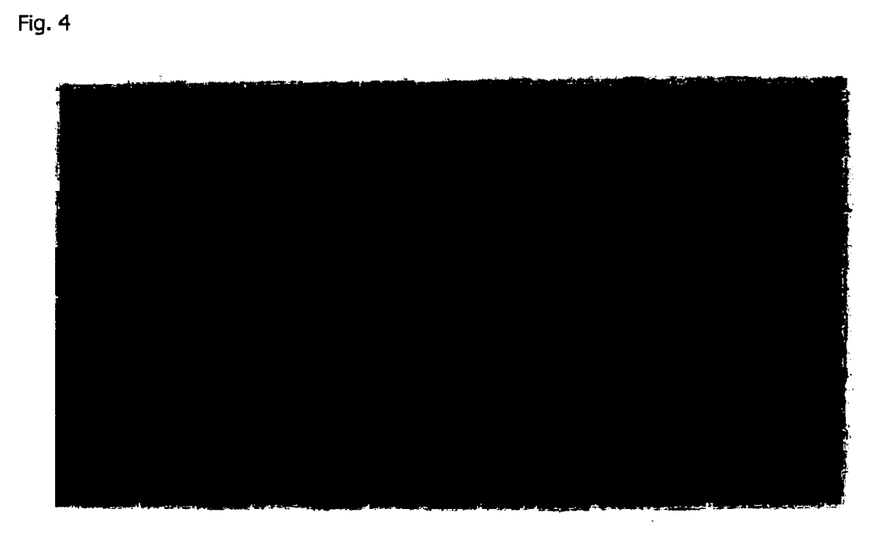
Figure 5:
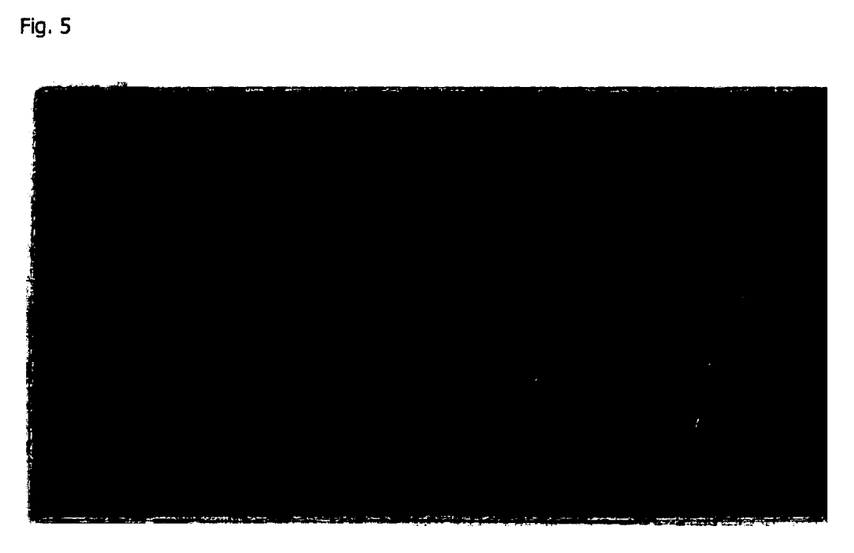
Figure 6:
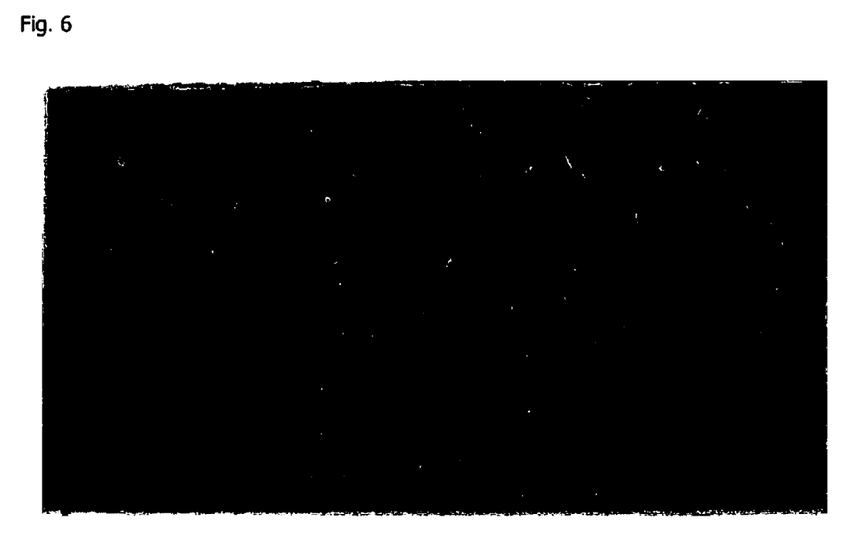
Figure 7:
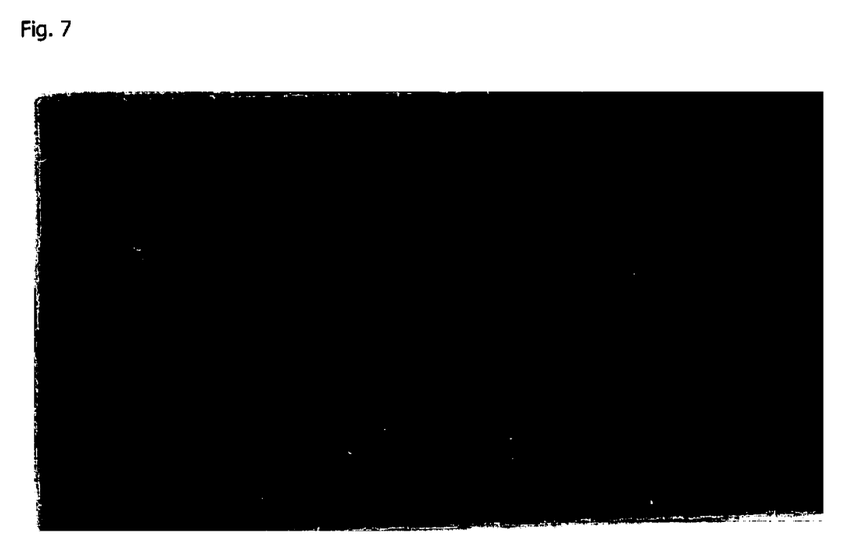

The methanol extract of old *platycodon* was treated with a concentration of 0.031, 0.062, 0.125, 0.25, 0.5 and 1 mg/ml, and the results of microscopic observation about the status of combination of cancer cell to laminin and cell morphology are shown in FIGS. 1a~1g. As shown in FIG. 1, in case of the control group, when DMSO used as a vehicle was added, cancer cells adhered on laminin, and in case the concentration of the methanol extract were 0.031 and 0.062 mg/ml, each 30% and 70% cells were found to be not adhered. When the concentration of methanol extract was greater than 0.125 mg/ml, 100% of cells kept their round cell morphology, unable to adhere to laminin. At the concentration of 0.5 mg/ml, 20–30% of the cells were damaged at the cell membrane, however the remaining 70–80% of cells kept their round cell morphology, unable to adhere to laminin, while at the concentration of 1 mg/ml damage of cell membrane of cancer cell have been observed. The results are shown in Table 4.

TABLE 4

| Mark of pictures | concentration of methanol extract (mg/ml) | Relative optical density at 570 nm | inhibition ratio against adhesion of laminin (%) |
|---|---|---|---|
| a | Control group | 1.00 | 0 |
| b | 0.031 | 0.71 | 30 |
| c | 0.062 | 0.22 | 70 |
| d | 0.125 | 0.00 | 100 |
| e | 0.250 | 0.00 | 100 |
| f | 0.500 | 0.00 | 100 |
| g | 1.000 | 0.00 | 100 |

Example 6

Immunity Augmenting Actions of Old *Platycodon*

The mice transplanted with complicated cancer or solid cancer were divided into group A (control group), group B (fed with ordinary *platycodon*), and group C (fed with old *platycodon*) and incubated for 3 weeks. The ratio of the immune cells such as NK-cell, T-cell, B-cell, Tc-cell, etc. in the blood of each mouse in each group, was examined using FAC Scan. In the case of complicated cancer, shown in Table 5, NK-cell shown direct anti-cancer effect, is 1.14% in group A, 1.52% in group B, and as high as 6.23%, about 5.5 times in group C which was fed with the old *platycodon*. Also, B-cell showed higher effect in group C than in group A or B, while T-Cell showed slightly lower level in group C but the fact that Tc-cell showed high level in group C indicates its anti-cancer effect.

And, for solid cancer, shown in Table 6, NK-cell is 3.6% in group A, 3.8% in group B, while it was as high as 4.55% in group C which was fed with old *platycodon*. B-cell showed lower level in the groups than in the control group, while T-cell and Tc-cell showed higher level in the groups than in the control group. These results indicate that it has the excellent anti-cancer effect.

TABLE 5

Immune Activity of Old Platycodon on complicated cancer

| | % Positive cells | | | |
|---|---|---|---|---|
| Treatment Groups | B cell (CD19) | T cell (CD3e) | Tc cell (CD8a) | NK cell (%) |
| A | 17.93 | 71.10 | 18.87 | 1.14 |
| B | 18.21 | 58.24 | 18.52 | 6.23 |
| C | 23.04 | 62.88 | 23.37 | 6.23 |

TABLE 6

Immune Activity of Old Platycodon solid cancer

| | % Positive cells | | | |
|---|---|---|---|---|
| Treatment Groups | B cell (CD19) | T cell (CD3e) | Tc cell (CD8a) | NK cell (%) |
| A | 43.85 | 49.77 | 12.97 | 3.6 |
| B | 34.18 | 49.82 | 12.32 | 3.80 |
| C | 36.92 | 53.19 | 13.10 | 4.55 |

Example 7

Effects of the Old *Platycodon* Extract and Herbal Medicine Product Containing *Platycodon* on Rheumatic Arthritis At about 20 days after injection of 0.6 mg/kg heat-killed 5. *Mycobacterium* histolyticm to the right sole of the feet of SD-rats, the degree of inhibition against inflammation was investigated by measuring the size of edema of both feet. The rats were divided into 7 groups and examined; feed group (group A) as a control group, not being caused edema, group B which was fed with 4 mg/day of predisolone as edema suppression agents, group C which was fed with 160 mg/day of ordinary *platycodon* extract, group D which was fed with 20 mg/day of 14 kinds of herbal medicine extract, group E which was fed with 160 mg/day of the old *platycodon* extract, group F which was fed with 40 mg/day of herbal medicine extract and 160 mg/day of the old *platycodon* extract. Each group was assigned to have 6 SD-rats. The results are shown in Table 7.

TABLE 7

| Experimental Groups | Edema suppression activity in the right foot (%) | Edema suppression activity in the left foot (%) |
|---|---|---|
| A | 100 | 100 |
| B | 84.5 | 83.8 |
| C | 12.6 | 13.2 |
| D | 26.7 | 26.2 |
| E | 67.5 | 68.3 |
| F | 85.8 | 85.0 |

It was observed that group E (fed with the old *platycodon* extract) and group F (fed with herb medicine and the old *platycodon* extract) showed excellent activity in suppressing edema. However, when the intake of the old *platycodon* extract was increased to 200 mg/kg, it did not show a significant activity and the highest activity which was observed was with the intake of 100–200 mg/kg. From the results of the examination of the edema suppression activity according to the intake amount, the highest activity was observed at 150 mg/kg.

The herbal medicine product manufactured using 20-year or older *platycodon* has not only excellent pharmacological effects and physiological activity compared with 2–4 year ordinary *platycodon*, but also shows excellent antibacterial activity against bacteria or protozoa, blood glucose lowering effect or lipid metabolism improving activity in serum or liver, inhibitory activity against the adhesion of cancer cells and immunity increasing activity compared with ordinary *platycodon*. Antibacterial agent, anti-inflammatory agent, antihyperlipidemia agent, anti-diabetes agent and anti-cancer agent manufactured from the extract of old *platycodon* have not only excellent pharmacological effects, but also no toxicity nor other side effects unlike the present chemotherapeutics Although the present invention has been described and illustrated with respect to exemplary embodiments thereof, it should be understood by those skilled in the art that the foregoing, and variations may be made therein and thereto without departing from the spirit and scope of the present invention.

What is claimed is:

1. A medicine manufactured using hot water extract of old *platycodon* manufactured by the steps of:
    a) preparing old *platycodon* powder by drying and grinding old *platycodon*;
    b) adding water to said old *platycodon* powder, performing extraction on the resultant liquid 2 times at a temperature of 90~100° C. for 4~6 hours, and filtering the resultant liquid.

2. The medicine of claim 1, wherein the medicine is an antibiotics.

3. The medicine of claim 1, wherein the medicine is an anti-inflammatory agent.

4. The medicine of claim 3, wherein the anti-inflammatory agent is for disease of rheumatic arthritis.

5. The medicine of claim 1, wherein the medicine is an anti-hyperlipemia agent.

6. The medicine of claim 1, wherein the medicine is an anti-diabetes agent.

7. The medicine of claim 1, wherein the medicine is an anticancer agent.

8. The medicine of claim 1, wherein the *platycodon* is 20-year or older perennial *platycodon*.

* * * * *